United States Patent [19]
Barta et al.

[11] Patent Number: 5,540,666
[45] Date of Patent: Jul. 30, 1996

[54] CANNULA SHIELD AND INJECTION SYRINGE SYSTEM

[75] Inventors: Helmut Barta, Vienna; Franz Moser, Deutsch Wagram; Walter Simonich, Vienna, all of Austria

[73] Assignee: Immuno Aktiengesellschaft, Vienna, Austria

[21] Appl. No.: 218,944

[22] Filed: Mar. 28, 1994

[30] Foreign Application Priority Data

Mar. 31, 1993 [AT] Austria ........................ 656/73
Mar. 31, 1993 [AT] Austria ........................ 657/93

[51] Int. Cl.⁶ ........................................ A61M 5/32
[52] U.S. Cl. ..................... 604/192; 604/198; 604/110
[58] Field of Search ........................... 604/192–199, 604/117, 263, 278, 240, 242, 243, 283, 905; 128/230, 919; 206/365

[56] References Cited

U.S. PATENT DOCUMENTS

| | | | |
|---|---|---|---|
| 3,073,307 | 1/1963 | Stevens | 604/192 |
| 3,306,291 | 2/1967 | Burke | 206/365 X |
| 3,889,673 | 6/1975 | Dovey et al. | 604/192 |
| 3,987,940 | 10/1976 | Tischlinger | 604/187 X |
| 4,281,653 | 8/1981 | Barta et al. | 604/192 |
| 4,500,310 | 2/1985 | Christinger | 604/228 |
| 4,642,104 | 2/1987 | Sakamoto et al. | 604/264 |
| 4,720,285 | 1/1988 | Pickhard | 604/192 |
| 4,735,311 | 4/1988 | Lowe et al. | 206/365 |
| 4,826,491 | 5/1989 | Schromm | 604/198 |
| 4,850,970 | 7/1989 | Sutherland | 604/117 |
| 4,871,355 | 10/1989 | Kikkawa | 604/198 |
| 4,872,552 | 10/1989 | Unger | 206/365 |
| 4,986,818 | 1/1991 | Imbert et al. | 604/192 |
| 5,085,647 | 2/1992 | Henderson et al. | 604/192 |
| 5,290,228 | 3/1994 | Uemura et al. | 604/90 |

FOREIGN PATENT DOCUMENTS

| | | |
|---|---|---|
| 242286 | 9/1965 | Austria . |
| 360139 | 5/1980 | Austria . |
| 848081 | 9/1952 | Germany . |
| 863799 | 3/1961 | United Kingdom . |
| 88/00478 | 1/1988 | WIPO . |

*Primary Examiner*—Randall L. Green
*Assistant Examiner*—V. Alexander
*Attorney, Agent, or Firm*—Foley & Lardner

[57] ABSTRACT

There is disclosed an injection syringe assembly comprising a cannula module including a two-part cannula shield device having a separate front cap, as well as a latched-in cannula holder in which a cannula is glued. In the mounted state, a plug-like cannula seal is received in the front cap and the cannula holding means is located forwardly of the syringe cone of a syringe body of an injection syringe. It is indirectly fastened to the syringe cone by aid of an elongated fastening portion of the cannula shield device. The cannula shield device includes two predetermined breaking points in order to be able to recognize immediately unauthorized manipulations at the syringe.

28 Claims, 1 Drawing Sheet

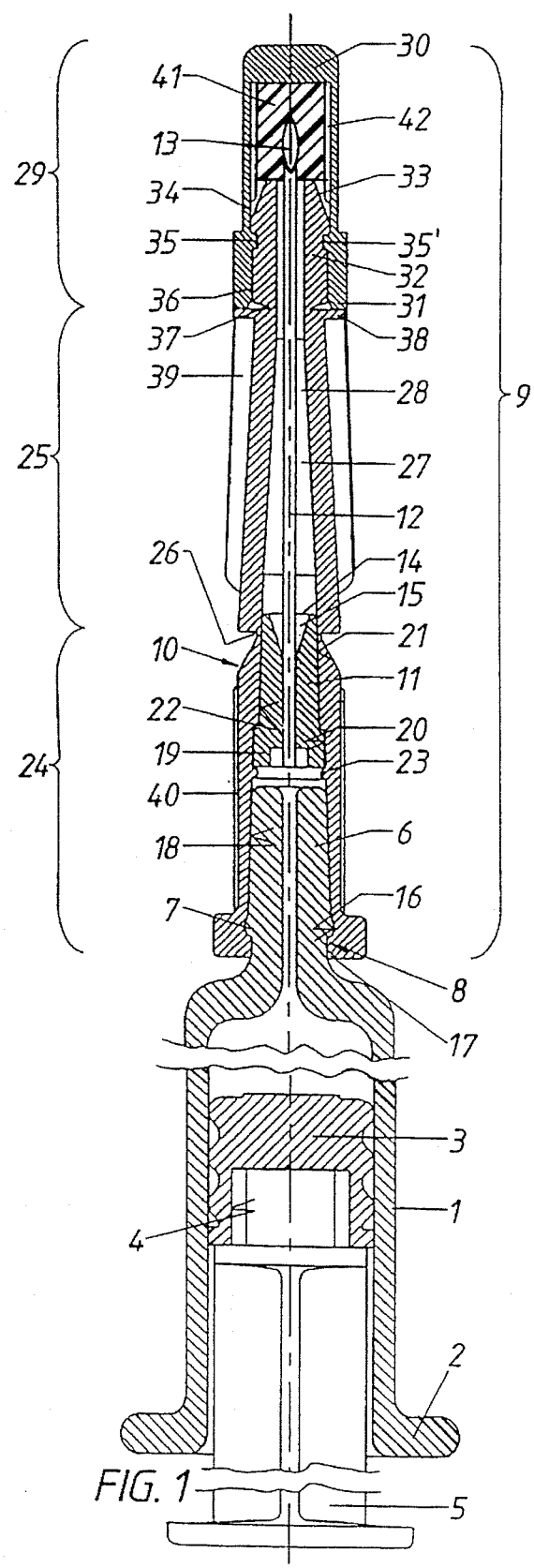
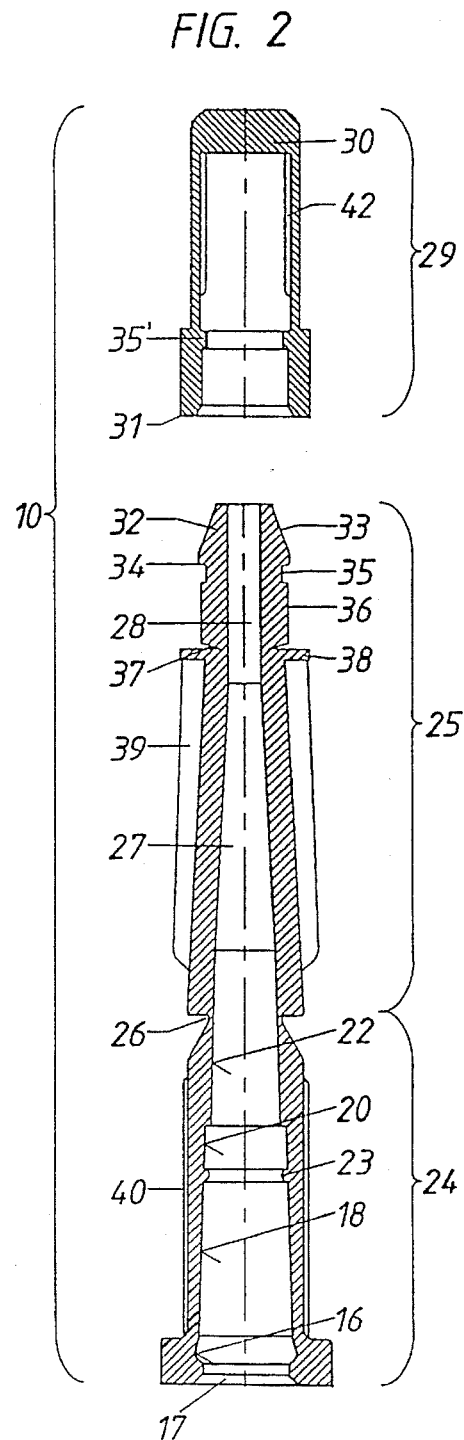
FIG. 1
FIG. 2

CANNULA SHIELD AND INJECTION SYRINGE SYSTEM

This application claims priority to Austrian patent application numbers A 656/93 and A 657/93, both filed on Mar. 31, 1993.

BACKGROUND OF THE INVENTION

1. Field of the Invention

This invention is directed generally to an improved injection syringe assembly, in particular, a disposable injection syringe assembly.

More particularly, this invention relates to a cannula shield device for an injection syringe, comprising a rear fastening portion provided for attachment to a syringe body and a forward sheath portion integrally connected therewith and separable therefrom, for instance, at a predetermined breaking point.

Furthermore, this invention relates to a cannula module including such a cannula shield device and a cannula received in a cannula holding means within the interior of the cannula shield device.

Also, the invention relates to an injection syringe comprising a syringe body and a cannula module of the above kind as well as, furthermore, a syringe body for such an injection syringe, including a hub for attaching a cannula module.

Finally, this invention is directed to a method of assembling and filling an injection syringe.

2. Description of Related Art

In AT-B-242 286 a cannula shield device comprising a rear fastening portion and a forward sheath portion is disclosed, both portions being connected via a predetermined breaking point. A separate cannula holding means firmly fixed in the cannula shield device is provided for attachment of the cannula. An inner cone is provided in the rear fastening portion for fastening the cannula shield device to a syringe body. However, with this cannula shield device no seal is provided for the cannula; instead, the cannula shield device is used, in particular, with an injection syringe in which a separate ampoule sealed by a membrane is inserted in a cylinder, the membrane being pierced through by a sharpened rear end of the cannula. However, providing a separate ampoule with a membrane as well as a rearwardly protruding sharpened cannula end is relatively expensive.

From U.S. Pat. Nos. 4,735,311, 4,986,818 and 5,085,647, disposable injection syringes are known, with which the cannula is rigidly mounted in a hub of the syringe body and a cannula shield device is placeable over the cannula, said cannula shield device including an internal channel conically narrowed towards the tip of the cannula and merging into a cavity widened in the region of the cannula tip. Into this widened cavity, a rubber plug is introducible into which the cannula tip projects and by which the forward opening of the cannula is tightly closed. The rubber plug, on the side of the cannula, is supported on an abutment surface of the cannula shield device. It is introduced through an opening corresponding to the internal diameter of the cavity and provided on the forward end of the cannula shield device, whereupon this opening is plastically deformed by deforming the forward end of the cannula shield device in a manner that the rubber plug is held in the cannula shield device such that it cannot get lost. Yet, in doing so, an opening remains on the forward end of the cannula shield device towards the cavity receiving the rubber plug. A comparable injection syringe having a cylindrical cannula shield device in which a plug-like cannula seal is inserted is known from DE-C-848 081.

With these known injection syringes, the cannula shield device is simply slipped on the forward end of the cannula-carrying part of the syringe body, optionally latching or snapping over an annularly protruding collar of the cannula-carrying part of the syringe body, for instance, according to U.S. Pat. No. 4,735,311. Hence results the problem that manipulations at the injection syringe will not be noticed; in particular, it will not be recognized whether the cannula shield device has already been removed and the injection syringe has already been used.

A cannula directly glued in the syringe body additionally involves the disadvantage of difficult manufacturing of the injection syringe, because the internal wall of the syringe body, as a rule, must be treated with a lubricant applied by evaporation at a elevated temperature. Yet, the adhesive by which the cannula is glued in the syringe body does not withstand such high temperatures without getting discolored, or destroyed, respectively. On the other hand, it is also difficult to provide a syringe body already treated with lubricant with a cannula, since a lubricant-treated surface no longer takes an adhesive.

The difficulty implied by an adhesive connection for the cannula directly to the syringe body in treating the internal wall of the syringe body with a lubricant, in particular, silicone (what is called "silicone-treating" of the syringe body internal wall), is avoided with the injection syringe according to AT-B- 360 139, i.a., by gluing the cannula in a cannula holding means to be placed on a syringe cone of the syringe body afterwards by means of a latch connection. To this end, the syringe body is formed with a peripheral annular groove in which hook- or nose-shaped latch elements provided on the rear slitted end of the cannula holding means engage.

Then, a cannula shield device is slipped on the externally conical cannula holding means.

However, the latch connection for the cannula holding means on the syringe cone involves problems for two reasons: Firstly, the cannula holding means, in respect of the glued-in cannula, is to be comprised of a relatively hard and stiff synthetic material, the latch elements, thus, being subject to relatively easy breaking and, moreover, a tight fit of the cannula holding means on the syringe cone being hardly obtainable, and secondly, the structure of the syringe cone is weakened by the annular groove incorporated therein such that the syringe cone can be broken off relatively easily. Furthermore, cracks may form in the hard plastics material of the cannula holding means, resulting in leakages. Again, the cannula shield device is not secured against unauthorized manipulations, since it is merely slipped on.

U.S. Pat. No. 3,889,673 describes a cannula shield device comprising a separate front cap latched on a sheath member surrounding the cannula. The reason for the cannula shield device being divided in two parts resides in that the syringe is rendered more suitable for various use purposes, wherein, on the one hand, only the front cap of the cannula shield device is removed in order to add a medicament through a nipple to a liquid contained in a bag and, on the other hand, the entire cannula shield device is removed if a larger cannula length is required for introduction into a medicament bottle. There is neither a sealing means for the syringe content nor the possibility of verifying premature manipulations at the syringe; rather is it possible without any difficulty to remove and reposition the entire cannula shield means, or at least the front cap, without being able to notice it later on.

Finally, an injection syringe having a needle shield cap is known from WO-A-88/00478, in which the cap portion proper is integrally connected, via a predetermined breaking point, with a base portion intended for attachment. The known needle shield cap is closed on its front side and is provided for a disposable syringe assembly in which a disc-shaped seal is provided on the front-side end of the syringe body itself. Therefore, when using the syringe, at first this sealing disc must be pierced through by axially displacing the cannula rearwardly, for which purpose kind of a spindle drive is provided. Such a configuration is extremely expensive and disadvantageous in terms of manufacture and assembly of the cannula module and of the entire injection syringe. Moreover, it is disadvantageous that, when setting the syringe into operation, the cap portion is allowed to be rotated relative to the base portion and to the syringe body only in one specific sense of rotation to rearwardly displace the cannula for piercing through the sealing disc after having separated the predetermined breaking point. If the cap portion erroneously is rotated in the wrong direction, it may happen that the cannula is moved too much forwardly and the syringe becomes unusable. In addition, the cannula holding means requires a particularly great length, since it must be equipped with a rotational locking means relative to the cannula shield device on its forward end. The cannula itself likewise must be particularly long and must be ground on its two ends. The double-ground cannula is cast in the cannula holding means, which involves complex manufacturing procedures. Piercing through the sealing disc may result in the separation of particles getting then into the vaccine. Consequently, partial or total obstruction of the cannula may occur. A further disadvantage of the known construction is to be seen in that considerable pressure may build up within the vaccine, e.g., due to temperature fluctuations, which may cause the vaccine to leave the cannula immediately upon piercing through the sealing disc.

SUMMARY OF THE INVENTION

It is an object of the invention to avoid the disadvantages of the known assemblies and to enable the simple manufacture and assembling of the individual components of the syringe assembly. In particular, also perfect sealing is to be ensured.

Another object of the invention is to provide for a high degree of safety against unauthorized manipulations at the syringe.

Furthermore, it is an object of the invention to be able to manufacture and assemble a cannula shield device or cannula module separately from the remainder of the syringe, wherein, consequently, the syringe body may be provided with a lubricant independent of the cannula and its fastening means, strictly aseptic manufacture being feasible.

Furthermore, the invention aims at rendering feasible the economic automatic assembling of the syringe as well as its filling under sterile conditions without any danger of contamination while having the option of filling the respective liquid or medicament into the syringe body without the addition of a preserving agent.

The cannula shield device according to the invention, of the initially defined kind is characterized in that a front cap closed on its front side and having an open rear end, which is provided as a separate component, is fastened or fastenable to the open forward end of the sheath portion facing away from the fastening portion, and that a plug-like cannula seal receiving the cannula tip is received in the front cap.

Accordingly, the cannula module according to the invention, of the initially defined kind is characterized in that the cannula, on its front side, protrudes beyond the open forward end of the sheath portion and projects into the interior of the front cap, and that the cannula, on its rear end, is firmly secured in the cannula holding means, which, in turn, firmly fits in the rear zone of the cannula shield device.

The core of the invention, thus, resides in the two-part design of the cannula shield device, comprising the sheath portion proper integral with the fastening portion, on the one hand, and a front cap fastened or fastenable thereto on the front side, on the other hand. Due to this two-part design, not only is an advantage achieved in terms of manufacture with respect to the simplified production of the components, for instance, by injection molding, but also a check of the presence and correct position of a cannula during mounting prior to putting on the front cap is rendered feasible. What is also important is the provision of the plug-like cannula seal in the front cap, this cannula seal being readily insertable into the front cap prior to attaching the front cap to the sheath portion. In the assembled state, the cannula pricks the cannula seal with its tip. Thus, a narrow, conically tapering internal bore advantageously may be obtained within the cannula shield device for guiding the cannula when slipping the cannula shield device on the cannula. In a manner conventional per se, a soft caoutchouc material, in particular, natural caoutchouc, of medical quality may be used as the material for the cannula seal.

In order to enable the simple attachment of the front cap onto the sheath portion, on the one hand, and to possibly prevent unauthorized lifting of the front cap, for instance, for the purpose of an undesired manipulation, on the other hand, it is advantageous if corresponding snap or latch connection elements are molded on the sheath portion and on the front cap, which are designed for placing the front cap on the sheath portion.

For the purpose of a tight connection between the front cap and the sheath portion, it is, furthermore, beneficial if the sheath portion, in the region of its forward end, comprises a front-side abutment surface for the rear end of the front cap. In this case, it is, furthermore, advantageous in terms of manufacture if the front-side abutment surface of the sheath portion is formed by the front face of a peripheral collar integrally molded with the remaining sheath portion. By the front cap abutting on the front-side abutment surface, a seal is created between the parts mentioned, which is liquid-tight up to relatively high pressures and also is dust-proof.

In order to recognize premature manipulation at the cannula shield means or its front cap, it would, for instance, be conceivable to provide a predetermined breaking point on the front cap connection elements; otherwise, the connection between front cap and sheath portion could be relatively firm, and, when manipulating at the front cap, the predetermined breaking point preferably provided between the sheath portion and the rear fastening portion could enter into operation and break so that any premature manipulation will be recognized. However, a particularly high rate of safety will be achieved if the front cap is allocated its own predetermined breaking point in the sheath portion, and, accordingly, it is particularly advantageous if a forward predetermined breaking point is provided on the sheath portion in the vicinity of the forward end thereof, yet at a distance from the point of attachment of the front cap. This forward predetermined breaking point suitably is designed such that it will break in case of unauthorized manipulation at the front cap before the rear predetermined breaking point between sheath portion and fastening portion has been separated.

The forward predetermined breaking point simply may be provided in that the collar, on whose forward front face the front cap abuts with its rear end, merges into a, for instance, generally cylindrical front cap carrying element via this forward predetermined breaking point.

The front cap as well as the remaining cannula shield device preferably are made of a relatively soft synthetic material, such as, for instance, polyethylene, wherein latching pressing of the front cap onto the sheath portion or, possibly, its front cap carrying element is feasible also if the front cap is closed on its rear end in the peripheral direction, i.e., has no axis-parallel longitudinal slits. In this connection, the desired latch connection is to be realized quickly and then practically no longer detachable may be obtained in a particularly advantageous manner by forming an annular latching groove in the forward end of the sheath portion, possibly on the front cap carrying element, which groove cooperates with a radially inwardly protruding latch projection provided on the rear end of the front cap, to undetachably fastening the front cap to the sheath portion.

With regard to a readily feasible, yet firm and tight as well as reliable connection between cannula shield device and cannula holding means, it has proved to be particularly advantageous if the fastening portion comprises an inner cone as well as an annular groove for receiving a cannula holding means equipped with a corresponding outer cone and a corresponding peripherally extending annular projection.

For the safe and tight support of the cannula shield device on the syringe body it has, furthermore, proved beneficial if a latching groove is provided internally in the rear fastening portion, which matches with an annular bead provided on a, for instance, conus-shaped hub of the syringe body. In this case, an additional advantage is achieved in that the syringe body, which, for instance, is made of borosilicate glass, is not weakened in the region of its hub, since an annular bead is provided there as a latching element instead of a peripheral annular groove as has been the case with earlier syringes.

As regards the cannula module according to the invention and, in particular, the fastening of the cannula in the cannula holding means, the cannula in the instant assembly simply may be glued in the cannula holding means. The cannula holding means simply may be of a relatively rigid, stiff material, such as a cellulose propionate, being surrounded by the relatively soft material, such as polyethylene, of the cannula shield device, in order to be indirectly fastened to the syringe body via the fastening portion of the cannula shield device. A conventional medical adhesive is used for gluing the cannula in the cannula holding means, and the cannula may be made, for instance, of chromium-nickel steel.

For readily gluing in the cannula while ensuring its safe support in the cannula holding means, it has, furthermore, proved beneficial if the cannula holding means comprises a conically widening adhesive take-up means on its forward front end. In this manner, gluing of the cannula in the cannula holding means is facilitated, the cannula, nevertheless, being sufficiently firmly fit within the cannula holding means even though it is not glued with the cannula holding means over its total length within the same.

A particular idea of the present invention has been that the fastening of the cannula to the syringe body be as rigid and undetachable as possible, wherein, however, the simple attachment of the cannula to the syringe body without causing damage to the cannula holding means be guaranteed despite the use of a correspondingly rigid cannula holding means - into which the cannula can be glued in a particularly simple manner, getting sufficient support for its use. In this connection, a firm and tight fit of the cannula holding means within the cannula shield device is of importance, it being advantageous if the cannula holding means is rigidly inserted in the cannula shield device surrounding the cannula with the cannula holding means having an outer cone and the cannula shield device having an inner cone corresponding to the external cone of the cannula holding means. Moreover, it is also beneficial if a peripherally extending annular projection is provided on the outer cone of the cannula holding means on its end facing the syringe body and the cannula shield device, in its inner cone, has a groove corresponding to this projection.

In order to facilitate the separation of the sheath portion of the cannula shield device when using the injection syringe, in particular, by rotation in one or the other sense, it is, furthermore, advantageous if the forward front side of the cannula holding means is located slightly in front of the predetermined breaking point enabling the separation of the sheath portion.

According to another aspect, the present invention also relates to an injection syringe comprising a syringe body and a cannula module according to the invention, as well as to a syringe body for such an injection syringe comprising a hub for attaching a cannula module according to the invention. It is apparent, already from the foregoing explanations of the instant syringe assembly, that the cannula holding means of the cannula module is to be connected with the syringe body not directly, but indirectly via the fastening portion of the cannula shield device. Accordingly, the injection syringe of the invention is characterized in that the cannula module, while arranging the cannula holding means immediately forwardly of a syringe cone provided on the syringe body, is put on the syringe cone by the fastening portion of its cannula shield device. In doing so, it is, furthermore, advantageous if the cannula module is latched with the fastening portion on the syringe body, a peripheral annular bead on the syringe cone engaging in an annular groove in the internal wall of the fastening portion. Here it is furthermore beneficial if the syringe cone of the syringe body, in its rear end, includes a peripherally extending groove following upon the annular bead and re-entrant relative to the annular bead and, preferably, also relative to the syringe cone, the cannula shield device being designed in a corresponding manner under formation of a snap or latch connection known per se. Furthermore, it is also advantageous if the external surface of the syringe cone is roughened, if desired partially, in order to counteract any torsional movement of the attached fastening portion when separating the sheath portion by rotation of the latter. Due to the cannula being fastened in a cannula holding means separate from the syringe body, it is possible to make the syringe body of a glass body whose inner wall provided with a lubricant is treated at a high temperature, advantageously with silicone at approximately 300° C.

The syringe body according to the invention accordingly is characterized in that a syringe cone provided with a peripheral annular bead is provided as said hub.

Accordingly, it is also advantageous if a syringe cone provided with an optionally partially roughened external surface is provided as said hub.

A particularly firm fit of the cannula module suitably is provided if the syringe cone, on its rear end, comprises a peripherally extending annular bead and a peripherally extending annular groove following upon the annular bead.

The present syringe assembly in an advantageous manner renders feasible aseptic manufacture and mechanical processing, in particular, in the form of what is called in-line assembly and filling, manual operations and possible risks of contamination, thus, being avoidable. Accordingly, the invention also contemplates an advantageous method of assembling and filling an injection syringe according to the invention, which method is characterized in that the syringe body internally is silicone-treated separately and subsequently is sterilized, that, independently thereof, a sterilized cannula module is assembled by gluing the cannula in the cannula holding means, inserting the cannula holding means with the cannula into the cannula shield device and putting the front cap provided with the plug-shaped cannula seal on the sheath portion after having checked the presence of a cannula in the correct position at the open end of the sheath portion, and that the cannula module is tightly attached to the syringe body under sterile conditions and, finally, the syringe is filled and closed on its rear end by inserting a plunger plug. The cannula module elements suitably are sterilized by radiation.

In the following, the invention will be explained in more detail by way of a particularly preferred exemplary embodiment illustrated in the drawing, to which it is, however, not limited. In detail:

BRIEF DESCRIPTION OF THE FIGURES

FIG. 1 is a longitudinal section through a disposable injection syringe; and

FIG. 2 is an explosive view of the pertaining cannula shield device, also sectioned longitudinally.

DESCRIPTION OF THE PREFERRED EMBODIMENTS

A cylindrical syringe body 1 made of glass has a flange 2 on its rear end. On this end, the syringe body 1 is closeable by a plunger plug 3 including a recess 4 into which an actuation rod 5 is insertable. On its forward end, the syringe body 1 ends in a syringe cone 6 which, on its rear end, comprises a slightly protruding peripherally extending annular bead 7 and a peripherally extending annular groove 8 following upon the annular bead 7. The syringe body 1, on the site of the annular groove 8, has a diameter that is smaller than that of the syringe cone 6 at its thickest point. Yet, this difference in diameter is only slight.

A cannula module 9 produced as a separate structural unit independently of the syringe body 1 is put on the syringe cone 6. This cannula module 9 comprises a cannula shield device generally denoted by 10, in which a cannula holding means or cannula holder 11 is rigidly inserted. A cannula 12 is glued in the cannula holding means 11, for which purpose the cannula holder 11, on its end facing the cannula tip 13, includes a funnel-shaped recess 14 widening towards the cannula tip 13 and intended to receive an adhesive 15. Advantageously, an adhesive suitable for medical purposes is applied as the adhesive.

The cannula holder 11 itself is made of a relatively rigid, stiff synthetic material, such as, for instance, cellulose propionate; the cannula 12 is made, for instance, of chromium-nickel steel. The cannula shield device 10, in turn, is made of a relatively soft synthetic material, such as, for instance, polyethylene or polypropylene. Therefore, it can be slipped over the syringe cone 6 and its annular bead 7 provided on the rear end thereof in a relatively simple manner and fastened by latching in the annular bead 7 by means of an annular groove 16 configured to correspond to the annular bead 7. On its rear end, the cannula shield device 10 is provided with an lead-in cone 17 facilitating slight widening of the cannula shield device 10 while being put on the syringe cone 6.

Sealing tightness between the syringe cone 6 and the rear end of the cannula shield device 10 is obtained by the cannula shield device 10 having an inner cone 18 designed to correspond to the syringe cone 6. The cannula holder 11 is anchored in the cannula shield device 10 closely forwardly of the end of the syringe cone 6 by a radially protruding annular collar 19 arranged on the rear end of the cannula holder 11 and engaging in a groove 20 of the cannula shield device 10 arranged to correspond to this collar 19. Again, sealing tightness between the cannula shield device 10 and the cannula holder 11 is obtained by the cannula holder 11 having an outer cone 21 and the cannula shield device 10 having an inner cone 22 arranged to correspond to the former.

The groove 20 receiving the collar 19, on its end facing the syringe cone 6, is closed by a small annular bead 23 radially protruding inwardly such that the cannula holder 11 is sufficiently fixed in the axial direction after having been pressed into the cannula shield device 10.

The cannula shield device 10 partially is formed by a fastening portion 24, which assumes a supporting function for the cannula holder 11 and also a supporting function in respect of the fastening to the syringe body 1. A sheath portion 25 is designed integral with this fastening portion 24, these two portions being interconnected via a predetermined breaking point 26. This predetermined breaking point 26 is formed by an extreme reduction of the wall thickness closely behind the forward end of the cannula holder 11. The sheath portion 25 has a conically tapering interior cavity 27 merging into a cylindrical interior cavity 28 in the direction towards the cannula tip 13. It is slightly shorter than the length of the cannula 12 such that the cannula tip 13, by its oblique ground faces, as a whole comes to lie externally of the sheath portion 25.

The cannula shield device 10 additionally comprises a front cap 29 including a forward closed front side 30 and an open rear end 31 by which it can be slipped over the end part 32 of the sheath portion 25. This end part 32, seen from its forward end, comprises a leading cone 33 followed by a short cylindrical section 34. The latter merges into an annular groove 35 into which an annular internal projection 35' of the front cap 29 may be latched. This groove 35 is followed by a cylindrical guide portion 36, which facilitates putting on the front cap 29.

The cylindrical guide portion 36 merges into a radially outwardly extending collar 38 via a predetermined breaking point 37 likewise formed by a circumferentially extending wall reduction. Departing from the collar 38, outwardly protruding picking ribs 39 extend closely to the predetermined breaking point 26 provided at the cannula holder 11 and serve to facilitate turning off the sheath portion 25 from the fastening portion 24. In doing so, the fastening portion 24 need not be held; yet, it also comprises protruding longitudinal ribs 40 enhancing the grip. Due to its conical clamping seat on the syringe body 1, the fastening portion 24 is sufficiently supported such that co-rotation of the same when removing the sheath portion 25, i.e., rotation of the fastening portion 24 relative to the syringe body 1, will be prevented. By roughening the external side of the syringe cone 6, the support of the fastening portion 24 on the syringe cone 6 may be further improved.

In the front cap 29, a cannula seal 41 is inserted, into which the tip 13 of the cannula 12 may be pricked such that the cannula 12 is closed on its forward end. This cannula seal 41 preferably is made of natural caoutchouc. It is inserted in the front cap 29 prior to attaching the front cap 29 to the sheath portion 25 and is held there on account of internally arranged ribs 42 protruding inwards in radial direction.

As is apparent from the drawing, the front cap 29 has such a length that its open end 31 abuts the peripheral collar 38 of the sheath portion 25. The size of the cannula seal 41 is dimensioned such that, with the front cap 29 put on the sheath portion 25, slight squeezing of the cannula seal 41 occurs in a manner so as to ensure the absolute tightness of the cavity 27, 28 enclosed by the sheath portion 25 relative to the outer atmosphere.

The annular groove 35 of the end part 32 of the cannula sheath 10 forming part of the front cap portion and the corresponding annular internal projection 35' of the front cap 29 are configured in a manner that latching of the front cap 29 is feasible without difficulty, yet detachment is no longer possible. If attempts are still made to detach it, the forward predetermined breaking point 37 will tear. If, upon tearing of the forward predetermined breaking point 37, attempts are made to re-place the front cap 29 on the cannula 12, the front cap 29 (and the end part 32 of the sheath portion 25 therein) will slightly spring off the collar 38 of the sheath portion 32 on account of the resilient properties of the cannula seal 41. Thus, an interstice will be immediately recognized between the end 31 of the front cap 29 and the collar 38, the user, thus, knowing that the front cap 29 has already been removed, i.e., manipulations have been carried out.

The advantage of the above-described structure resides in that the cannula 12 entirely is surrounded by structural elements that cannot be removed from the cannula 12 without such manipulation being apparent at once. It is also essential that the cannula seal 41 is arranged to be fully protected towards outside such that manipulations at the cannula seal 41 are not possible, either, without being immediately recognized from outside.

Machine manufacturing of the cannula module 9 suitably is feasible in the following manner:

At first, the two elements of the cannula shield device 10, i.e., the front cap 29 and the sheath portion 25 integrally connected with the fastening portion 24, are produced by injection molding, advantageously under appropriate cleanroom conditions. On a separate assembly machine, the cannula 12 is glued in a cannula holding means 11 produced in the same manner, by an appropriate adhesive. After this, the cannula holding means 11, together with the cannula 12, is pressed into the cannula shield device 10 until the envisaged sealing cone connection has been obtained at 21, 22.

The cannula 12, by its ground tip 13, protrudes beyond the forward end of the sheath portion 24. Subsequently, suitable optical inspection of the presence of a cannula 12 and checking whether the cannula 12 has assumed its correct position—tip 13 forward—are effected. If it is found out that the cannula is not in the right position by its ground faces, this part is discarded as inferior. Then, a continuity check of the cannula 12 is effected. Subsequently, the front cap 29, together with the cannula seal 41 previously pressed therein, is pressed over the end part 32 until the snap connection (35, 35') latches. After this, welding of the cannula module 9 into a package takes place and, finally, sterilization by radiation may be effected.

The syringe bodies 1 of glass are made independently of the above manufacturing and assembling procedure. They are delivered in trays and mechanically taken out of the trays. After washing, the syringe bodies 1 are silicone-treated inwardly. Subsequently, they are put into magazines and moved through a sterilizing tunnel (approximately 300° C.) within the same.

After sterilization, the syringe bodies 1 are removed from the magazines and supplied to a cannula module press-on station. The radiation-sterilized cannula modules 9 are latchingly pressed on the syringe bodies 1, a tight connection between these two elements thus being achieved.

In a consecutive station, the syringe body 1 is filled, whereupon the plunger 3 is inserted. In this state, the disposable injection syringe already is tightly closed. It is conveyed out of the sterile zone by a conveying system and placed back into the trays.

What we claim is:

1. A cannula shield device for sealingly enclosing a cannula of an injection syringe having a syringe body to which said cannula having a cannula tip is fastened, said cannula shield device comprising:

a shield body including a rear fastening portion having means for connection with the syringe body, and a forward sheath portion integrally and separably connected with said rear fastening portion, wherein said forward sheath portion has (i) an open forward end facing away from said rear fastening portion and (ii) is separable from said rear fastening portion by a predetermined breaking point;

a front cap which has a closed forward front end and an open rear end, said open rear end of said front cap and said open forward end of said forward sheath portion including means for fastening said front cap onto said open forward end of said forward sheath portion;

a plug-like sealing means enclosed in said front cap and arranged to receive and seal the cannula tip prior to use of the injection syringe.

2. A cannula shield device as set forth in claim 1, wherein said sheath portion and said front cap further comprise a snap or latch connection means that (A) is molded and configured for attachment of said front cap to said sheath portion and (B) comprises a fastening means located on a rear inner region of said front cap and on a forward outer region of said sheath portion.

3. A cannula shield device as set forth in claim 2, wherein said corresponding snap or latch connection means comprise an annular latching groove formed in said forward end of said sheath portion and a radially inwardly protruding latching projection provided on said rear end of said front cap and configured to cooperate with said annular latching groove for undetachably fastening said front cap to said sheath portion.

4. A cannula shield device as set forth in claim 1, wherein said sheath portion, in the region of its forward end, comprises a front-side abutment surface for said rear end of said front cap.

5. A cannula shield device as set forth in claim 4, wherein said sheath portion further comprises a collar integrally formed with said sheath portion and having a front face forming a front-side abutment surface of the sheath portion.

6. A cannula shield device as set forth in claim 5, wherein said sheath portion further comprises a front cap carrying means, said collar merging into said front cap carrying means via said forward predetermined breaking point.

7. A cannula shield device as set forth in claim 1, further comprising a cannula holding means provided with an outer cone and a peripherally extending annular projection and wherein said fastening portion has an inner cone and an annular groove correspondingly configured to receive said cannula holding means by said outer cone and said peripherally extending annular projection.

8. A cannula shield device as set forth in claim 1, wherein said shield body further comprises a latching groove provided inwardly of said rear fastening portion.

9. A cannula module comprising a cannula and a cannula holding means, said cannula having a cannula tip in said cannula holding means, a cannula shield device surrounding said cannula, said cannula shield device comprising:

a shield body including a rear fastening portion having means for connection with a syringe body, and a forward sheath portion integrally and separably connected with said rear fastening portion, wherein said forward sheath portion has (i) an open forward end facing away from said rear fastening portion and (ii) is separable from said rear fastening portion by a predetermined breaking point;

a front cap which has a closed forward front end and an open rear end, said open rear end of said front cap and said open forward end of said forward sheath portion including means for fastening said front cap onto said open forward end of said forward sheath portion;

a predetermined breaking point adjoining said forward end and said front cap; and a plug-like sealing means enclosed in said front cap and arranged to receive and seal said cannula tip prior to use of the injection syringe;

wherein said cannula protrudes beyond said open forward end of said sheath portion on the front side thereof so as to project into the interior of said front cap and is firmly fastened within said cannula holding means by its rear end, said cannula holding means, in turn, being firmly fit within said cannula shield device in a rear zone thereof.

10. A cannula module as set forth in claim 9, wherein said cannula is glued in said cannula holding means.

11. A cannula module as set forth in claim 9, wherein said cannula holding means has a forward front end provided with a conically widened adhesive-reception space.

12. A cannula module as set forth in claim 9, wherein said cannula holding means is rigidly inserted in said cannula shield device surrounding said cannula and comprises an outer cone, said cannula shield device having an inner cone configured to correspond to said outer cone of said cannula holding means.

13. A cannula module as set forth in claim 12, wherein said outer cone of said cannula holding means has a syringe-body facing end and a peripherally extending annular outer cone projection provided on said syringe-body facing end, said cannula shield device, on its inner cone, having an inner cone groove corresponding to said outer cone projection.

14. A cannula module as set forth in claim 9, wherein said cannula holding means has its forward front face located slightly forwardly of said predetermined breaking point.

15. A cannula module as set forth in claim 9, wherein said cannula holding means is made of rigid synthetic material and said cannula shield device is made of a softer synthetic material.

16. A cannula module as set forth in claim 15, wherein said cannula holding means is made of cellulose propionate.

17. A cannula module as set forth in claim 15, wherein said cannula shield device is made of synthetic material selected from the group consisting of polyethylene and polypropylene.

18. An injection syringe assembly comprising a syringe body and a cannula module comprising a cannula having a cannula tip, a cannula shield device surrounding said cannula, and a cannula holding means accommodating said cannula within said cannula shield device, said cannula shield device comprising:

a shield body including a rear fastening portion having means for connection with said syringe body, and a forward sheath portion integrally and separably connected with said rear fastening portion wherein said forward sheath portion has (i) an open forward end facing away from said rear fastening portion and (ii) is separable from said rear fastenining portion by a predetermined breaking point;

a front cap which has a closed forward front end and an open rear end, said open rear end of said front cap and said open forward end of said forward sheath portion including means for fastening said front cap onto said open forward end of said forward sheath portion;

a predetermined breaking point adjoining said forward end and said front cap; and a plug-like sealing means enclosed in said front cap and arranged to receive and seal said cannula tip prior to use of the injection syringe;

wherein said cannula protrudes beyond said open forward end of said sheath portion on the front side thereof so as to project into the interior of said front cap and is firmly fastened within said cannula holding means by its rear end, said cannula holding means, in turn, being firmly fit within said cannula shield device in a rear zone thereof; and wherein said syringe body comprises a syringe cone and said cannula module is put on said syringe cone by said fastening portion of said cannula shield device under arrangement of said cannula holding means immediately forwardly of said syringe cone.

19. An injection syringe assembly as set forth in claim 18, wherein said syringe cone further comprises a peripheral annular syringe cone bead and an annular latching groove provided in said fastening portion in its internal wall, and wherein said cannula module is latched in said syringe body by its fastening portion by said peripheral annular syringe cone bead engaging said annular latching groove.

20. An injection syringe assembly as set forth in claim 19, wherein said syringe body ends in said syringe cone which, on its rear end, further comprises a peripherally extending syringe cone groove following upon said annular syringe cone bead in a manner re-entrant relative to said annular syringe cone bead, said cannula shield device being configured in a corresponding manner thus forming a snap or latch connection.

21. An injection syringe assembly as set forth in claim 20, wherein said peripherally extending syringe cone groove is re-entrant also relative to said syringe cone.

22. An injection syringe assembly as set forth in claim 18, wherein said syringe cone has its external surface at least partially roughened.

23. An injection syringe assembly as set forth in claim 18, wherein said syringe body is comprised of a glass body having an internal wall provided with a lubricant and treated at a high temperature.

24. An injection syringe assembly as set forth in claim 23, wherein said internal wall is treated with silicone at approximately 300° C.

25. An injection syringe assembly comprising a syringe body and a cannula module comprising a cannula having a cannula tip, a cannula shield device surrounding said cannula, and a cannula holding means accommodating said cannula within said cannula shield device, said cannula shield device comprising:

a shield body including a rear fastening portion having means for connection with said syringe body, and a forward sheath portion integrally and separably connected with said rear fastening portion wherein said forward sheath portion has (i) an open forward end facing away from said rear fastening portion and (ii) is separable from said rear fastening portion by a predetermined breaking point;

a front cap which has a closed forward front end and an open rear end, said open rear end of said front cap and said open forward end of said forward sheath portion including means for fastening said front cap onto said open forward end of said forward sheath portion;

a predetermined breaking point adjoining said forward end and said front cap; and a plug-like sealing means enclosed in said front cap and arranged to receive and seal said cannula tip prior to use of the injection syringe;

wherein said cannula protrudes beyond said open forward end of said sheath portion on the front side thereof so as to project into the interior of said front cap and is firmly fastened within said cannula holding means by its rear end, said cannula holding means, in turn, being firmly fit within said cannula shield device in a rear zone thereof;

wherein said syringe body comprises a hub and said cannula module is put on said hub by said fastening portion of said cannula shield device under arrangement of said cannula holding means immediately forwardly of said hub; and wherein said hub is configured for fastening said cannula module and is formed by a syringe cone provided with a peripheral annular syringe cone bead.

26. A syringe body as set forth in claim 25, wherein said syringe cone further comprises said peripheral annular syringe cone bead and further comprising a peripherally extending annular syringe cone groove following upon said peripheral annular syringe cone bead.

27. An injection syringe assembly comprising a syringe body and a cannula module comprising a cannula having a cannula tip, a cannula shield device surrounding said cannula, and a cannula holding means accommodating said cannula within said cannula shield device, said cannula shield device comprising:

a shield body including a rear fastening portion having means for connection with said syringe body, and a forward sheath portion integrally and separably connected with said rear fastening portion wherein said forward sheath portion has (i) an open forward end facing away from said rear fastening portion and (ii) is separable from said rear fastening portion by a predetermined breaking point;

a front cap which has a closed forward front end and an open rear end, said open rear end of said front cap and said open forward end of said forward sheath portion including means for fastening said front cap onto said open forward end of said forward sheath portion;

a predetermined breaking point adjoining said forward end and said front cap; and a plug-like sealing means enclosed in said front cap and arranged to receive and seal said cannula tip prior to use of the injection syringe;

wherein said cannula protrudes beyond said open forward end of said sheath portion on the front side thereof so as to project into the interior of said front cap and is firmly fastened within said cannula holding means by its rear end, said cannula holding means, in turn, being firmly fit within said cannula shield device in a rear zone thereof;

wherein said syringe body comprises a hub and said cannula module is put on said hub by said fastening portion of said cannula shield device under arrangement of said cannula holding means immediately forwardly of said hub; and wherein said hub is configured for fastening said cannula module and is formed by a syringe cone provided with a roughened external surface.

28. A syringe body as set forth in claim 27, wherein said syringe cone further comprises a peripheral annular syringe cone bead and further comprising a peripherally extending annular syringe cone groove following upon said peripheral annular syringe cone bead.

* * * * *